(12) United States Patent
Beachy et al.

(10) Patent No.: US 8,076,073 B2
(45) Date of Patent: *Dec. 13, 2011

(54) CHOLESTEROL AND HEDGEHOG SIGNALING

(75) Inventors: Philip A. Beachy, Baltimore, MD (US);
Jeffrey A. Porter, Belmont, MA (US);
Michael K. Cooper, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 554 days.

This patent is subject to a terminal disclaimer.

(21) Appl. No.: 10/442,435

(22) Filed: May 20, 2003

(65) Prior Publication Data

US 2003/0207853 A1 Nov. 6, 2003

Related U.S. Application Data

(60) Division of application No. 09/954,727, filed on Sep. 11, 2001, now abandoned, which is a continuation of application No. 09/250,785, filed on Feb. 12, 1999, now Pat. No. 6,288,048.

(60) Provisional application No. 60/074,714, filed on Feb. 13, 1998.

(51) Int. Cl.
*C12Q 1/00* (2006.01)
*C12Q 1/68* (2006.01)

(52) U.S. Cl. ............ 435/6.1; 435/4; 435/6.13; 435/6.17
(58) Field of Classification Search .................. None
See application file for complete search history.

(56) References Cited

U.S. PATENT DOCUMENTS

| 5,789,543 | A | | 8/1998 | Ingham et al. ............... 530/350 |
| 5,844,079 | A | | 12/1998 | Ingham et al. ............... 530/350 |
| 6,027,882 | A | * | 2/2000 | Scott et al. .......................... 435/6 |
| 6,057,091 | A | * | 5/2000 | Beachy et al. ..................... 435/4 |
| 6,214,794 | B1 | | 4/2001 | Beachy et al. ..................... 514/2 |
| 6,288,048 | B1 | | 9/2001 | Beachy et al. ............... 435/962 |

OTHER PUBLICATIONS

Beachy et al Multiple Roles of Cholesterol in Hedgehog Protein Biogenesis and Signaling Cold Springs Harbor Symposia on Quantitative Biology, vol. LXII, 1997, pp. 191-204.*
Porter et al., Cholesterol Modification of Hedgehog Signaling Proteins in Animal Development, Science, vol. 274, 1996, pp. 255-259.*
Beachy et al (Cholesterol Modification of Hedgehog Signaling Proteins in Animal Development. Science, 1996. 274:255-259).*
Teratogen. (2003). In Webster's New world Medical Dictionary. Retrieved Dec. 12, 2006, from http://www.xreferplus.com/entry/2440176.*
Shiota et al (Teratogenic drugs inhibit the differentiation of fetal rat limb buds grafted in athymic (nude) mice. Reproductive Toxicology. 1990;4(2):95-103. (abstract only)).*
Tanabe, et al (Induction of motor neurons by Sonic Hedgehog is independent of floor plate differentiation. Current Biology, 1995. 5(6):651-658).*
Gaffield et al. Toxins Reviews, (1996), vol. 15, No. 5, pp. 303-326.*
Ressler et al. Nature Genetics, (1996) vol. 14, 357-360.*
Porter, et al., Cholesterol Modification of Hedgehog Signaling Proteins in Animal Development, Oct. 11, 1996, Science, vol. 274, pp. 255-259.
Keeler, Teratogenic Effects of Cyclopamine and Jervine in Rats, Mice, and Hamster, 1975, Proceedings of the Society of Experimental Biology and Medicine, vol. 149, pp. 302-306.
Campbell, et al., Comparative Effects of Retinoic Acid and Jervine on Chondrocyte Differentiation, 1987, Teratology, vol. 36, pp. 235-243.
Beachy et al., Multiple Roes of Cholesterol in Hedgehog Protein Biogenesis and Signaling Cold Springs Harbor Symposia on Quantitative Biology, vol. LXII, 1997, pp. 191-204.

* cited by examiner

*Primary Examiner* — Janet L Epps-Smith
(74) *Attorney, Agent, or Firm* — DLA Piper LLP (US)

(57) ABSTRACT

The present invention sterol-modified hedgehog polypeptides and functional fragments thereof. Methods of identifying compositions which affect hedgehog activity based on inhibition of cholesterol modification of hedgehog protein are described. In one aspect of the invention, the method provides a means for affecting cholesterol biosynthesis or transport in a cell comprising contacting a cell with an effective amount of a compound that affects hedgehog, thereby affecting cholesterol biosynthesis or transport. The effect may be inhibition or stimulation of cholesterol biosynthesis or transport.

9 Claims, 7 Drawing Sheets

FIG. 1

FIG. 2A with detergent without detergent

FIG. 2B cells　medium　cells　medium

ND HEDGEHOG
CHOLESTEROL AND HEDGEHOG SIGNALING

RELATED APPLICATIONS

This application is a Divisional of U.S. application Ser. No. 09/954,727, filed Sep. 11, 2001 now abandoned, which is a Continuation of U.S. application Ser. No. 09/250,785, filed Feb. 12, 1999, which issued as U.S. Pat. No. 6,288,048, which claims priority under 35 U.S.C. Section 119(e) to U.S. Provisional Application Ser. No. 60/074,714 filed Feb. 13, 1998. All of which are incorporated by reference into the disclosure of this application.

BACKGROUND OF THE INVENTION

1. Field of the Invention

This invention relates generally to the field of protein processing and protein signalling pathways and specifically to two novel proteins having distinct activities, which are derived from a common hedgehog protein precursor.

2. Related Art

Over the past decade, extracellular protein signals encoded by several gene families have emerged as central players in coordinating cell behavior and thus generating pattern during animal development. Members of the hedgehog (hh) gene family in particular are notable for their association with several well-studied patterning activities. In *Drosophila*, where hh was discovered and isolated, patterning functions include specification of positional identity within developing segments and appendages. In vertebrate embryos, function of the hh family member Sonic hedgehog (Shh) is associated with the patterning influences of notochord and prechordal plate mesoderm on spinal cord and brain, as well as on other surrounding structures Shh expressed in mesoderm at the posterior margin of the developing vertebrate limb bud also plays a central role in controlling limb outgrowth and patterning. The patterning functions of hh proteins have been extensively studied (see Hammerschmidt et al. 1997 for a recent general review), and novel functions continue to emerge.

SUMMARY OF THE INVENTION

This article presents a selective view of the hh protein biogenesis and signaling pathways, with particular attention paid to the involvement of the abundant neutral lipid cholesterol. One role for cholesterol is as a covalent adduct for the biologically active form of the hh protein (Hh), which is formed as a product of an autoprocessing reaction that entails internal cleavage. Cholesterol attachment restricts the spatial deployment of the Hh signal, thus influencing the pattern of cellular responses in developing tissues. Here we summarize our studies of the Hh autoprocessing reaction, and of the role of cholesterol in this reaction. We also summarize more recent studies suggesting that, in addition to its role in Hh signal production, cholesterol has an essential role in mediating the response to the Hh signal within target cells. This role is revealed by genetic or drug-induced perturbations of cholesterol homeostasis that render target tissues unresponsive to the Hh signal.

In yet another embodiment, the invention provides a method for identifying a compound which affects hedgehog activity comprising incubating the compound with hedgehog polypeptide, or with biologically active fragments thereof, or with a recombinant cell expressing hedgehog, under conditions sufficient to allow the components to interact; and determining the effect of the compound on hedgehog activity or expression. For example, cholesterol level (e.g., biosynthesis or transport) is measured as an inidicator of hedgehog activity. In one aspect of the invention, the method provides a means for affecting cholesterol biosynthesis or transport in a cell comprising contacting a cell with an effective amount of a compound that affects hedgehog, thereby affecting cholesterol biosynthesis or transport. The effect may be inhibition or stimulation of cholesterol biosynthesis or transport.

DESCRIPTION OF THE FIGURES

FIG. 1. Autoprocessing of the Hedgehog protein precursor. Following signal sequence cleavage, the Hedgehog precursor (Hh) undergoes an autoprocessing reaction that entails cleavage between the Gly and Cys residues within a tripeptide, Gly-Cys-Phe, that is conserved among all Hh proteins; this cleavage is accompanied by attachment of cholesterol to the carboxy-terminus of the amino-terminal product. Whereas the amino-terminal domain is active in signaling, the carboxy-terminal domain mediates the autoprocessing reaction, and the resulting modification by cholesterol influences the tissue distribution of signaling acitivity. As indicated, amino acid sequence conservation among orthologues of the Hh family is greater within the amino-terminal as compared to the carboxy-terminal domain. Crystallographic analysis of the amino-terminal domain of Shh protein revealed striking similarity in folded structure of a portion of this domain to the catalytic domain of D,D carboxypeptidase, a zinc hydrolase from Streptomyces that acts on cell wall components (Dideberg et al. 1982; Hall et al. 1995; Murzin 1996); the significance of this similarity and the role of this putative hydrolase in Shh signaling are not known. Not shown in this figure, N-linked glycosylation of carboxy-terminal sequences has been reported within the carboxy-terminal domain of Shh (Bumcrot et al. 1995), but the glycosylation site is not uniformly conserved among Hh orthologues and its significance is unknown.

FIG. 3. Hh autoprocessing and protein self-splicing are initiated by formation of a thioester intermediate. As described in the text, Hh autoprocessing (A) and protein self-splicing (B) are both inititated by formation of a thioester in place of a main-chain peptide. The reactions differ in the second step, which for Hh entails attack of the thioester intermediate by cholesterol. For self-splicing proteins, the second nucleophile is the side chain of the first residue in the carboxy-terminal extein (C extein); the resulting three-branched intermediate is then resolved to give rise to the free intein and ligated N and C exteins. For simplicity, proton transfers implicit in the activation of nucleophiles or of leaving groups are omitted from this scheme.

FIG. 4. Evolutionary lineage of proteins containing Hint domains. Hint domains are found within three distinct protein families: the self-splicing proteins, the Hedgehog family of signaling proteins, and a novel family of *C. elegans* proteins of unknown function. In the self-splicing proteins an endonuclease domain is inserted within a peripheral loop of the Hint domain (Duan et al. 1997; Hall et al. 1997). In Hh proteins, a sterol recognition region (SRR) appended to the carboxy-terminus of the Hint domain is required for cholesterol addition; in the absence of SRR sequences, only the first step of thioester formation occurs. The Hint domains of the C. elegans proteins are more closely related to those of the Hh family, but SRR sequences are replaced by other sequences of variable length, tentatively referred to as the adduct recognition region (ARR). Eleven C. elegans proteins that contain Hint domains have been identified thus far (at 80% completion of the C. elegans genomic sequence); this family can be subdivided further into two homologous groups based on the presence of two unrelated types of sequences present within the amino-terminal domains of these proteins.

FIG. 5. Inhibition of cholesterol biosynthesis by the plant steroidal alkaloid, jervine. Sterols were extracted and analyzed by HPLC from COS7 cells metabolically labelled with [3H]-mevalonic acid in the presence or absence of jervine, a teratogenic plant steroidal alkaloid. In the presence of 28=|M jervine, radiolabelled cholesterol levels were reduced and another radiolabelled sterol was found to accumulate. On the basis of its retention time in this reverse phase HPLC method (Rodriguez and Parks 1985), this abnormal sterol is tentatively identified as zymosterol, an intermediate in the cholesterol biosynthetic pathway FIG. 6. Proteins with sterol sensing domains. Four proteins containing a sterol sensing domain (SSD) are schematically depicted. The cylinders denote predicted transmembrane helices and the SSD of each protein is enclosed within the rectangle formed by the dashed lines. As indicated by the shading, the homology between Patched (Ptc) and the Niemann-Pick C disease protein (NP-C) extends beyond the SSD to include all twelve of the Ptc transmembrane domains. In the case of HMG CoA reductase, the topology of these transmembrane segments was experimentally determined (Olender and Simoni 1992; Roitelman et al. 1992). The topology of Ptc shown is as suggested by Goodrich et al. (1996), and that of SCAP as suggested by Brown and Goldstein (1997). The proposed topology of the NP-C protein is based upon sequence analysis presented by Carstea et al. (1997) and the homology to Ptc; not shown are several transmembrane domains that are weakly predicted to exist in the human but not the mouse protein. The arrowhead after the first transmembrane domain of NP-C denotes a possible site of signal sequence cleavage as suggested by Carstea et al. (1997). The drawings only crudely approximate the extent of loops between transmembrane domains and are not intended to convey structural information. The labelling within these loops indicates the presence of the catalytic domain in carboxy-terminal portions of HMG CoA reductase, of four repeats of the WD protein-protein interaction domain in the carboxy-terminal portion of SCAP (Hua et al. 1996), and a region in the first loop of NP-C that is tightly conserved among all NP-C homologues from various species (Carstea et al. 1997; Loftus et al. 1997).

DESCRIPTION OF THE INVENTION

Results and Discussion

Hedgehog Protein Autoprocessing

Figure 1:
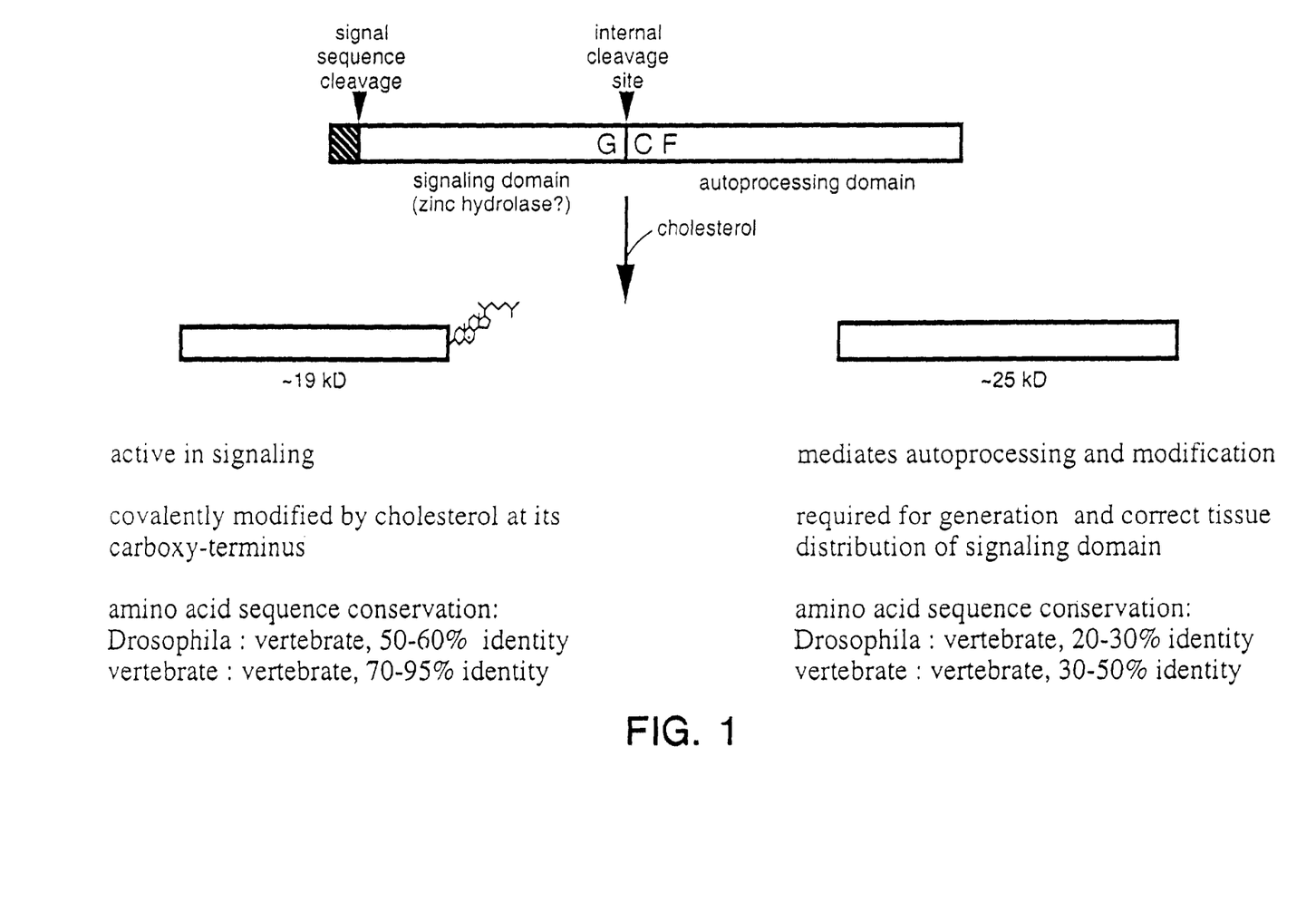

FIG. 1 presents a view of Hh biosynthesis which, although largely derived from studies of *Drosophila* Hh, likely applies to Hh proteins from all species. As suggested by genetic studies (Mohler 1988) and as predicted from sequence analysis (Lee et al. 1992; Mohler and Vani 1992; Tabata et al. 1992; Tashiro et al. 1993), the Hh protein enters the secretory pathway and is cleaved following a signal sequence located near the amino terminus (Lee et al. 1992). From earliest examination in in vitro translation experiments, the *Drosophila* Hh protein also revealed a propensity to undergo cleavage at another internal site (Lee et al. 1992); antibodies specifically directed against amino- or carboxy-terminal epitopes confirmed that the predominant forms of endogenous Hh protein correspond to the products of this internal cleavage (Lee et al. 1994). The internal cleavage depends upon carboxy-terminal Hh sequences and can be observed with purified recombinant protein in vitro, thus indicating the operation of a self-directed processing activity (Lee et al. 1994).

Further in vitro analysis of this cleavage demonstrated that it occurs between the Gly and Cys residues within a conserved Gly-Cys-Phe tripeptide (Porter et al. 1995). This information permitted ectopic expression in transgenic *Drosophila* of constructs encoding either the amino-terminal or the carboxy-terminal cleavage products (Hh-N and Hh-C, respectively), and these studies demonstrated that biological signaling activity resides entirely within the precisely truncated Hh-N fragment (Porter et al. 1995). Similar transgenic experiments also demonstrated that mutations within Hh-C that interfere with processing but do not alter Hh-N sequences nevertheless block Hh function (Lee et al. 1994; Porter et al. 1995). Thus, whereas Hh-N suffices for signaling activity, Hh-C sequences are required to generate the active amino-terminal signaling domain from precursor via autoprocessing (FIG. 1). Consistent with these conclusions, all molecularly characterized hh mutations in *Drosophila* either directly affect the Hh-N signaling domain or otherwise appear to block release of the signaling domain from precursor by affecting the Hh-C autoprocessing function (Porter et al. 1995).

Biological Role of Autoprocessing

Figure 2A:
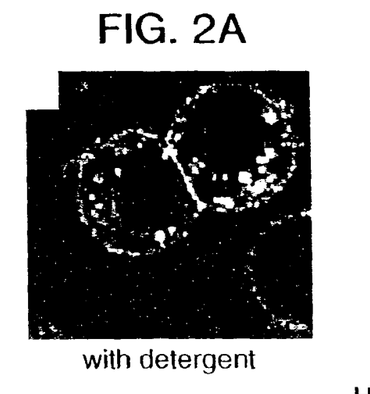
FIG. 2. Cell surface association of the amino-terminal domain Indirect immunofluorescence staining revealed a prominent cell-surface association of amino-terminal epitopes (A,B) with the plasma membrane; this staining was observed in the absence of detergent permeabilization, indicating localization to the cell surface. The Western blot in (C) shows amino-terminal domain expression from full-length Hh protein (Hh-Np; lanes 1,2) or from a construct with a chain termination codon at the cleavage site (Hh-N; lanes 3,4). Hh-Np is retained by cells within the culture whereas Hh-N is nearly quantitatively released into the medium. The greater mobility of Hh-Np relative to Hh-N is characteristic of processed Hh amino-terminal domains.
Figure 2B:
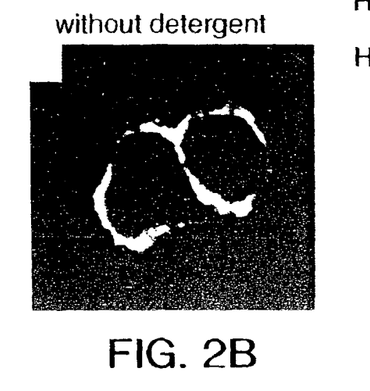
Figure 2C:
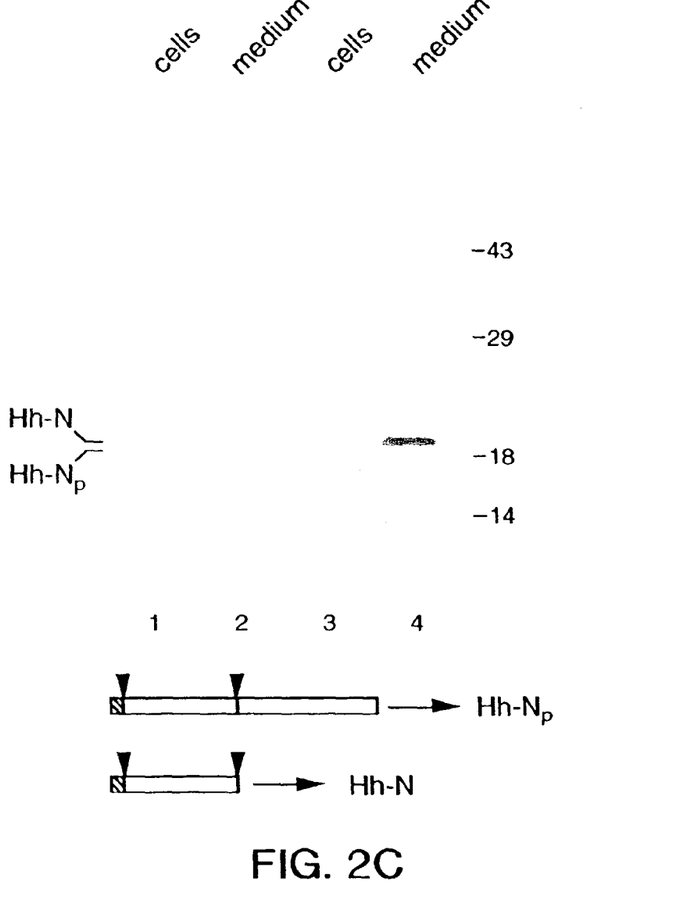

Since the cleavage products of the Hh precursor are the predominant forms observed in vivo, the occurrence of the autoprocessing event appears not to be regulated. What then is the raison d'etre of autoprocessing? The answer to this question began to emerge from studies in cultured cells which demonstrated that processed amino-terminal domain protein generated from precursor remains tightly associated with the cell surface (Lee et al. 1994; FIGS. 2a,b). In contrast, protein expressed from a construct lacking the autoprocessing domain is almost quantitatively released into the culture medium (Porter et al. 1995; FIG. 2c). Autoprocessing thus is associated with tethering of the amino-terminal signaling domain to the cell surface. Amino-terminal domain protein derived by processing of the Hh precursor is designated Hh-Np, to distinguish it from amino-terminal domain derived from a truncated construct (Hh-N).

As would be expected for a potent secreted signal whose expression is spatially restricted within segments, autoprocessing and cell surface tethering play an important role in segmental patterning (Porter et al. 1996a). This role was revealed by comparing the effects of localized expression of Hh-N or Hh-Np in transgenic *Drosophila* embryos: when activated at the normal sites of hh transcription, transgenes expressing Hh-Np, which is also the form of the endogenous protein signal, showed no significant alterations in the normal segmental patterns of gene expression or cuticle formation. In contrast, similar localized expression of transgenic Hh-N caused disruption of segmental patterning equivalent to that caused by ubiquitous high-level expression of Hh protein. Autoprocessing thus appears to restrict the spatial distribution of Hh signaling activity, and immunofluorescence studies indeed confirm that Hh-N more readily diffuses from expressing cells to surrounding cells than does Hh-Np (Porter et al. 1996a). These immunofluorescence studies also revealed a difference in subcellular localization within expressing cells, with Hh-Np sequestered in large punctate structures in basolateral domains of epidermal cells. Hh-N protein from the truncated construct in contrast lacks this type of punctate localization and instead appears to be freely secreted to the apical surface of expressing cells within the epidermal epithelium (Porter et al. 1996a). The functional significance of this processing-dependent localization to the basolateral domain of expressing cells within the epidermal epithelium is not yet known.

The biological role of autoprocessing in vertebrates is particularly well illustrated by the role of Shh in neural tube patterning. Shh protein is processed similarly to the Hh protein (Bumcrot et al. 1995; Chang et al. 1994; Ekker et al. 1995; Lai et al. 1995; Porter et al. 1995; Roelink et al. 1995), and the normal cell surface association of the amino-terminal fragment also is processing-dependent (Bumcrot et al. 1995; Porter et al. 1996b; Roelink et al. 1995). Loss of Shh gene function in mouse embryos results in failure to differentiate floor plate cells and motor neurons (Chiang et al. 1996). Induction in naive neural plate explants of these and other ventral cell types by recombinant Shh-N protein occurs in a concentration-dependent manner, with motor neurons induced at low concentrations and floor plate cells induced at the expense of motor neuron fates at higher concentrations (Ericson et al. 1997; Marti et al. 1995; Roelink et al. 1995). In other explant experiments with embryonic tissues as inducers, structures such as the notochord can only induce floor plate cells in a contact-dependent manner (Placzek et al. 1993) whereas motor neuron induction does not require such contact (Yamada et al. 1993). The ability to circumvent contact-dependence with high concentrations of soluble Shh-N protein suggests that one role for modification and surface association of the signaling domain is to generate large concentration differences between local and distant sites, with consequent sharp distinctions between the cell types induced. Consistent with this idea, the Shh signaling domain is found predominantly on the surface of notochord cells and embryonic floor plate normally forms only in close proximity to the notochord.

The Autoprocessing Reaction

Given the striking differences in diffusibility and patterning activity of Hh-N and Hh-Np, it was not surprising to find accompanying physical differences. As compared to Hh-N, Hh-Np displays a slight difference in electrophoretic mobility (FIG. 2c), a dramatic increase in hydrophobic character, a greater mass associated with the carboxy-terminal fragment of CNBr digestion, and an insensitivity to digestion by carboxypeptidase (Porter et al. 1996a). These data together indicate that Hh-Np carries a covalently attached lipophilic adduct at its carboxy-terminus whose addition depends upon the autoprocessing activity of the carboxy-terminal domain. The presence of this adduct accounts for the tethering of Hh-Np to the cell surface, since the lipid adduct would be expected to partition preferentially into the lipid bilayer.

Despite information about its mass and other properties, the identity of the lipid adduct could not be determined directly because quantities of purified Hh-Np sufficient for chemical analysis proved difficult to obtain. Identification of the adduct therefore relied ultimately on a mechanistic understanding of the in vitro processing reaction and its use as an assay to identify a lipid capable of participating in the auto-processing reaction Initial insight into the autoprocessing reaction derived from the observation that the kinetics of cleavage in vitro were independent of starting protein concentration, indicating an intramolecular mechanism (Porter et al. 1995). From a limited number of proteins known to auto-process by an intramolecular mechanism, a particularly strong analogy could be drawn to prohistidine decarboxylase (van Poelje and Snell 1990), which is capable of undergoing intramolecular cleavage with either a Cys or Ser residue at the position immediately following the scissile bond; Hh autocleavage also could be observed in vitro, albeit inefficiently, if a Ser residue replaced the normal Cys (Porter et al. 1996a). Contemporaneously with our studies of Hh autoprocessing, the self-splicing proteins have also emerged as intramolecular processing proteins with Ser or Cys residues at the site of cleavage (Xu and Perler 1996); we now know that the similarities between Hh and self-splicing proteins extend beyond mechanism to include sequence and structure (Hall et al. 1997; see below).

Figure 3A:
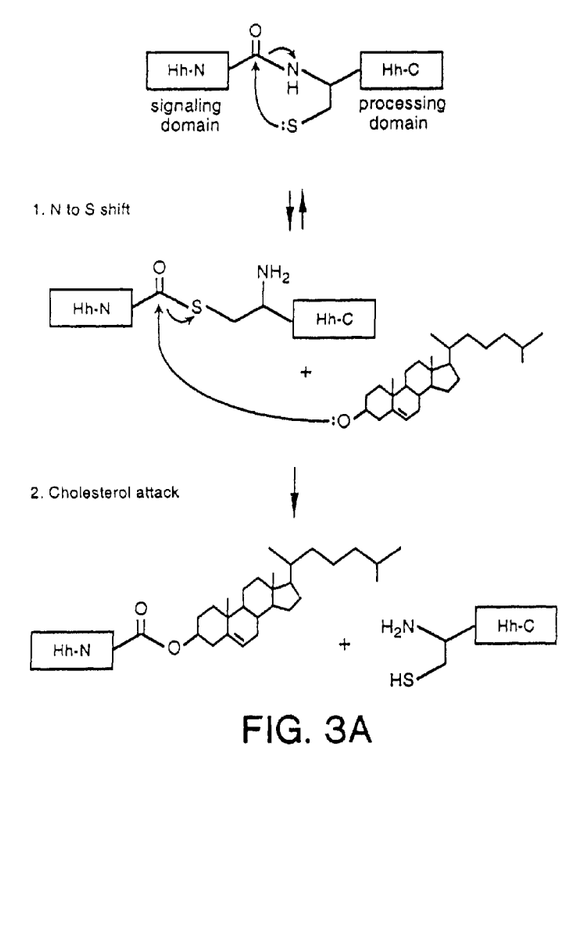

The feature common to all of these autoprocessing reactions is initiation by attack of a nucleophilic side chain upon the preceding carbonyl, with displacement of the peptide amine and formation of an ester or thioester intermediate. As seen in FIG. 3A, this is the first step of the Hh autoprocessing reaction, with a labile thioester replacing the main chain peptide bond between amino- and carboxy-terminal domains (Porter et al. 1996a; Porter et al. 1995). The second step of the Hh autoprocessing reaction involves attack upon the same carbonyl by a second nucleophile, displacing the sulfur and severing the connection between Hh-N and Hh-C. The requirement for a second nucleophile in vitro can be met by a high concentration either of a thiol-containing molecule or of another small molecule with nucleophilic properties at neutral pH; these small nucleophiles can be shown to form covalent adducts to the amino-terminal product of the in vitro cleavage reaction (Porter et al. 1996a).

Of some interest in the in vitro studies of Hh autoprocessing was the use of Cys-initiated peptides as nucleophile in the second step: the initial linkage between the peptide and the amino-terminal product is a thioester, which can then rearrange to form an amide bond by reversal of the steps involved in thioester formation during the first part of the reaction (Porter et al. 1996a). The net effect of these reactions is the ligation of a Cys-initiated peptide at the site of cleavage, and is analogous to the recent use of a chemically synthesized thioester intermediate for peptide ligation (Dawson et al. 1994).

Cholesterol Modification in Vitro and in Vivo

To account for the lipid modification in Hh-Np, the in vivo reaction was presumed to occur with the participation of an endogenous lipid carrying the second nucleophilic moiety. This presumption led to use of the in vitro reaction as an assay which was applied to fractionated cell lipids, leading to the identification of cholesterol as a neutral lipid that at relatively low concentrations could supply the requirement for a nucleophile in the second step (Porter et al. 1996b). Cholesterol thus stimulates the in vitro autoprocessing reaction and forms a covalent linkage to the amino-terminal product of cleavage reaction. This linkage is sensitive to base treatment, consistent with formation of an ester with the oxygen of the 3° hydroxyl of cholesterol. Confirming this role for cholesterol in vivo, [3H]-cholesterol was observed to label Hh-Np or Shh-Np expressed in *Drosophila* or in mammalian cultured cells, and this label could be removed by base treatment (Porter et al. 1996b; K.E.Y, J.A.P. and P.A.B., unpublished results). The label hydrolyzed from Hh-Np was further analyzed and shown to display chromatographic behavior identical to that of cholesterol, indicating that the in vivo adduct is cholesterol and not some other sterol derivative.

A somewhat surprising finding in the metabolic labelling experiments with mammalian cells is the apparent linkage of cholesterol to several other mammalian proteins. There is little evidence at present regarding the identity and function of these proteins, or the mechanism of attachment of cholesterol. We have found that the cholesterol can be removed from these proteins by base treatment, suggestive of an ester linkage like that resulting from Hh autoprocessing (K.E.Y, J.A.P. and P.A.B., unpublished results).

Thioesters as Intermediates in Protein Modification

The use of a Cys-derived thioester as an intermediate is a theme common to several other acyl transfers that result in covalent modifications of proteins. Following formation of the initial thioester in these systems, the acyl portion of the thioester (the acceptor, corresponding to Hh-N; see diagram in Table 1) can receive the final modification directly or alternatively may be transferred to other thiols in one or more subsequent steps before receiving the final modification (Table 1). The ubiquitin cascade represents such a reaction with multiple intermediates, whose role is to attach ubiquitin to proteins destined for degradation by the proteasome (Hochstrasser 1996). The acyl group for these thioesters is supplied by the carboxy-terminal Gly of ubiquitin, and the thiols come from Cys side chains in three distinct classes of enzymes. The first of these, E1, forms the initial thioester in an ATP-consuming reaction. Then, through trans(thio)esterification reactions, the ubiquitin forms thioesters sequentially with E2 and E3 enzymes, before final transfer to the e amine of a Lys side chain. The protein receiving ubiquitin in the resulting amide linkage is thus marked for degradation.

The a-macroglobulin proteinase inhibitors and the C3, C4, and C5 complement proteins represent members of an ancient superfamily that use an intrachain thioester as a "spring loaded" functionality that can be triggered for covalent attachment to target molecules (Chu and Pizzo 1994). The intrachain thioester is formed by thiol attack of a Cys side chain on the amido group of a Gln side chain. The final adducts in the case of the complement proteins are nucleophiles on the surface of cells to be targeted for lysis. In the a-macroglobulin case, the final adduct is a nucleophile on a protease to be inactivated, which is targeted to a-macroglobulin through the presence of multiple cleavage sites for proteases of various specificities.

In the examples just discussed, the acyl group contributing to the thioester intermediate derives either from another protein or from an amino acid side chain. In contrast, the acyl group in the Hh thioester intermediate is linked to a main chain carbonyl, and the thioester therefore replaces an amide bond within the peptide backbone. Other proteins likely to utilize main chain ester or thioester intermediates in autoprocessing reactions include prohistidine decarboxylase and certain members of the Ntn hydrolase family that are processed by an intramolecular mechanism (Brannigan et al. 1995; Guan et al. 1996). The Ntn (N-terminal nucleophile) hydrolases are structurally related enzymes that are autoprocessed with internal cleavage, leaving the active site nucleophile as the amino-terminal residue. The role of these reactions appears to be activation of a precursor protein and there is no net addition of a modifying adduct. Thus, although the prohistidine decarboxylase reaction was of heuristic value in understanding the mechanism of Hh autoprocessing, there is no evidence of any evolutionary relationship between Hh autoprocessing domains and either prohistidine decarboxylase or Ntn hydrolase proteins.

Ester Intermediates in Proteins Containing the Hint Domain

Figure 3B:
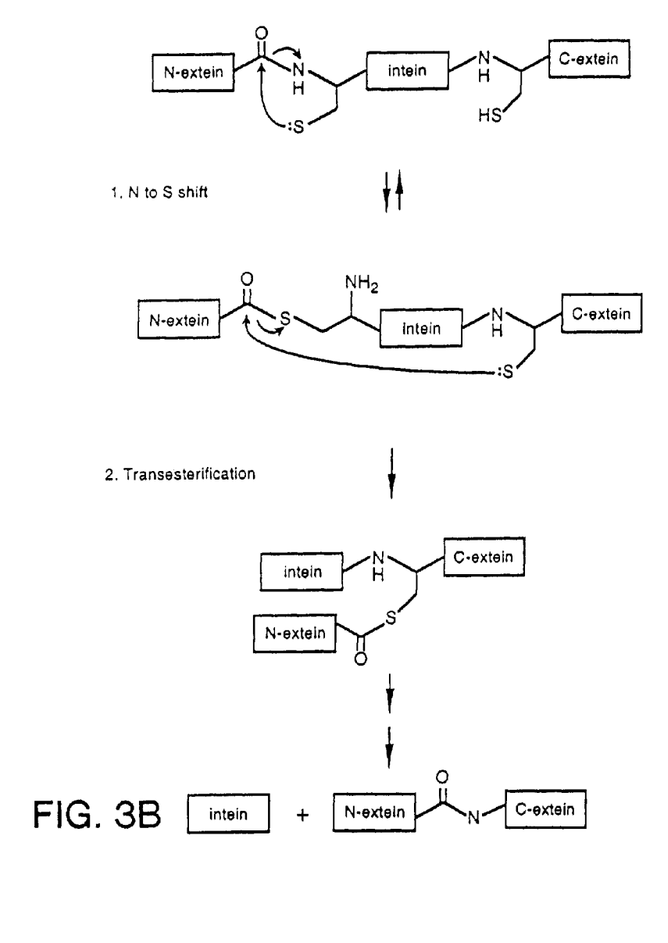

In contrast, Hh proteins are evolutionarily related to two other groups of proteins, the self-splicing proteins and a group of novel nematode proteins containing Hh-C-like sequences. The self-splicing proteins undergo a reaction in which an internal portion of the protein, termed an intein, is excised and amino- and carboxy-terminal flanking regions, termed exteins, are ligated to form the mature protein (Perler et al. 1994) Inteins are found inserted into a wide variety of archacal, bacterial, chloroplast, and yeast proteins. The intein portion mediates the protein splicing reaction and typically also contains an endonuclease thought to act at the DNA level in mediating movement of intein coding sequences. Similar to Hh autoprocessing, the protein splicing reaction is initiated by intramolecular attack of a hydroxyl or thiol upon the preceding carbonyl, and the resulting ester or thioester intermediate replaces the peptide bond at the amino-terminal extein/intein boundary (Xu and Perler 1996); FIG. 3). Unlike Hh proteins, the second nucleophilic attack in the protein self-splicing reaction involves the side chain of another Ser or Cys residue several hundred residues downstream. The resulting branched protein intermediate ultimately resolves into the ligated exteins and the free intein protein (FIG. 3).

Nematode proteins with Hh-C-like sequences were identified by searching for homology within the *C. elegans* genomic sequence database. At ~80% completion of the *C. elegans* genome, eleven putative proteins with homology to the Hh-C autoprocessing domain have been identified (Burglin 1996; Hall et al. 1997; Porter et al. 1996a; R. Mann, X. Wang, and P.A.B., unpublished data). As in the Hh family, the Hh-C-like domain is located at the carboxy-terminus of these proteins and is preceded by an amino-terminal domain bearing a signal sequence. The amino-terminal domains of these nematode proteins, however, bear no sequence similarity to Hh-N. Instead, they resemble each other and can be divided into two families. The structures of these proteins suggest the possibility that they are secreted and undergo autoprocessing; a preliminary study of one family member in *Drosophila* cultured cells indeed demonstrates cleavage at the junction between amino- and carboxy-terminal domains (Porter et al. 1996a).

The level of amino acid sequence identity between these nematode proteins and Hh ranges from 24 to 32% in a region approximately corresponding to the amino-terminal ⅔ of Hh-C. This same region of Hh-C also can be aligned with inteins, although alignment is complicated by the presence of sequences corresponding to the endonuclease (Dalgaard et al. 1997; Hall et al. 1997; Pietrokovski 1997). The level of amino acid identity between Hh-C and inteins with endonuclease sequences removed is ~10%, but most of the residues known to be essential for Hh-C processing activity are conserved.

A common evolutionary origin for these protein families is further indicated by a domain with a common fold that is present in the crystal structure of a portion of Hh-C and in the crystal structure of the 454 residue intein protein PI-SceI (Duan et al. 1997; Hall et al. 1997). Two additional domains not present in the Hh-C fragment are present in the intein structure: one of these is the endonuclease and the other is thought to aid in DNA binding. Remarkably, both of these additional domains are inserted into peripheral loops of the common domain, with little apparent effect upon its three dimensional fold. The crystallized Hh fragment contains the amino-terminal 151 residues of Hh-C, of which the first 145 residues are well-ordered in the crystal structure; these residues correspond to the region conserved in the nematode proteins. This domain alone suffices for thioester formation, as indicated by the ability of a Hh protein truncated after this point to undergo cleavage in the presence of DTT (Hall et al 1997), and this domain has been referred to as the Hint module (Hedgehog, intein).

Although the Hint module in Hh-C suffices for the first step of autoprocessing, at least some part of the 63 carboxy-terminal residues missing in the crystallized fragment are required for the second step of cholesterol addition (Hall et al. 1997). Because of its apparent role in sterol addition, this 63 residue region d us to be acutely aware of the is referred to as SRR, for sterol recognition region. No clear alignment can be made between SRR and sequences within the nematode family, however, and sequences in these nematode proteins that extend carboxy-terminal to the Hint domain are tentatively designated ARR, for adduct recognition region. The differences in sequence between the SRR of Hh proteins and the ARR regions of nematode gene family members raises the possibility that molecules other than cholesterol may participate in the processing reaction and form novel protein-modifying adducts.

Figure 4:
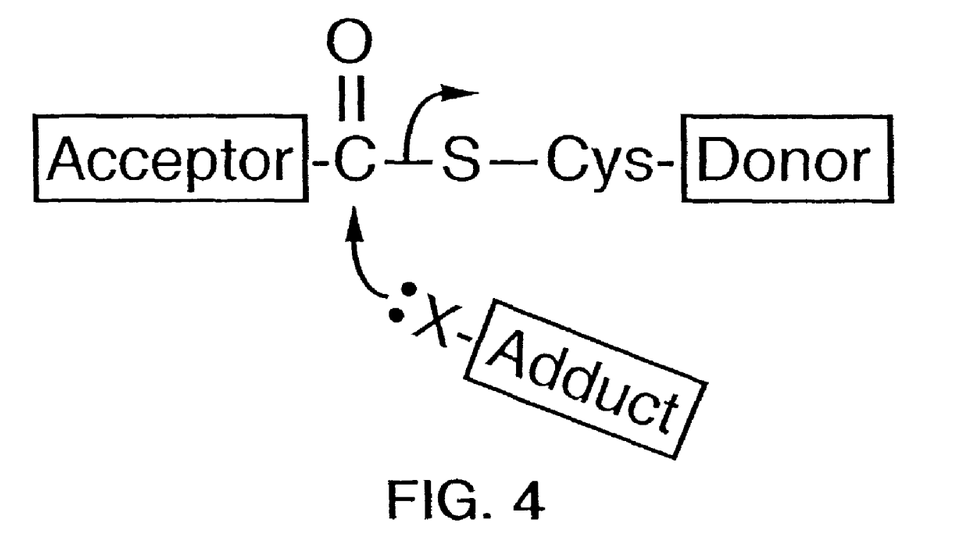

From these sequence and structure relationships, a plausible evolutionary history can be constructed in which all three protein groups diverged from an ancestral Hint domain (Hall et al. 1997; see FIG. 4). In one branch, the ancestral intein was formed by insertion of an endonuclease into a Hint domain and by adjustment (or preservation) of the chemistry to insure that the second nucleophilic attack is made intramolecularly by the side chain of a downstream residue. In a second branch, Hh proteins were formed by association of a Hint domain with amino-terminal domains of the Hh and nematode proteins. The sequence of events leading to formation of these proteins is not known. One possibility is that the Hint and SRR modules may have been assembled into a cholesterol transfer unit prior to association with the Hh signaling domain; alternatively, the Hint module might have been inserted within a preassembled protein comprising a signaling domain and the SRR precursor. In the second scenario, the SRR precursor in the preassembled protein might have served some function related to sterol recognition, such as membrane association. Similarly, several scenarios are possible in assembly of the nematode proteins. The possibility also exists that additional proteins will be found in which the Hint module initiates novel splicing or transfer reactions.

Cholesterol Synthesis Inhibitors and Holoprosencephaly

One of the most striking aspects of the Shh loss-of-function phenotype in mice (Chiang et al. 1996) is its resemblance to holoprosencephaly (HPE), a term applied to a spectrum of human developmental malformations characterized by a loss of midline structures in the forebrain and face. In its most severe form, as seen in Shh −/− mice, HPE is associated with a cyclopic eye positioned beneath a proboscis consisting of fused nasal chambers (Cohen and Sulik 1992). Abnormal features of brain anatomy, for which the syndrome is named, include an absence of ventral forebrain structures and development of remaining forebrain structures as a single fused vesicle. Experimental manipulations of amphibian embryos carried out more than 60 years ago led to an understanding of cyclopia as a consequence of disrupting the influence normally exerted by prechordal plate mesoderm upon forebrain neuroepithelium (Adelmann 1936b; Adelmann 1936a; Mangold 1931). This influence is required for bilateral subdivision of the early eye field; in its absence the eye field remains continuous across the midline, resulting in cyclopia and the loss of such ventral forebrain derivatives as the pituitary and the optic chiasm.

Shh expression in the prechordal mesoderm underlying the neural plate can first be detected in mid-streak mouse embryos (Chang et al. 1994; Echelard et al. 1993), a stage that coincides with or just precedes the requirement for prechordal plate signaling. All of these studies therefore are consistent with the view that Shh constitutes or contributes to the midline signal that passes from the prechordal plate mesoderm to forebrain neural plate, in a manner analogous to that in which Shh from the notochord induces regionalization and morphogenesis of the spinal cord. Recent studies indeed have demonstrated that an autosomal dominant form of human HPE is caused by mutations in the human Shh gene (Belloni et al. 1996; Roessler et al. 1996). The mutations described would be expected to cause a loss of Shh function, indicating that in contrast to the mouse Shh mutation, which is entirely recessive (Chiang et al. 1996), human Shh function is haploinsufficient. Consistent with this interpretation, the malformations associated with heterozygous human Shh mutations are variable, even among individuals carrying the same allele, and are far less severe than those in the homozygous mouse Shh mutation (Chiang et al. 1996).

Given this association of HPE with mutations in the Shh gene, a reasonable supposition would be that HPE could also be caused by other perturbations of the Shh signaling pathway Of particular interest to us, in view of the role of cholesterol in Hh autoprocessing, were a series of observations published beginning more than thirty years ago which noted that HPE-like malformations can be induced by treatment of pregnant rats with the drugs Triparanol, AY 9944R, and BM 15.766 (Dehart et al. 1997; Roux 1966; Roux 1964; Roux et al. 1979). These drugs inhibit enzymes of cholesterol biosynthesis and cause an abnormal accumulation of desmosterol (Triparanol) or of 7-dehydrocholesterol (AY 9944R and BM 15.766), which are the immediate precursors in alternate biosynthetic routes to cholesterol.

Genetic Perturbations of Cholesterol Synthesis and Transport

Further links between cholesterol and vertebrate embryonic development are provided by several mouse and human mutations affecting cholesterol synthesis or transport. Smith-Lemli-Opitz Syndrome (SLOS) is an autosomal recessive human genetic disease characterized by numerous developmental defects including microcephaly, pituitary agenesis, limb and genital abnormalities, and defects of the heart, kidneys, and pancreas (Opitz 1994; Salen et al. 1996; Tint et al. 1994). These patients lack the activity of 7-dehydrocholesterol reductase, the same enzyme inhibited by AY 9944R or BM 15.766, and as a consequence have abnormally low serum cholesterol levels and accumulate 7-dehydrocholesterol. Approximately 5% of SLOS patients display signs of HPE, with malformations that tend toward the milder end of the spectrum (Kelley et al. 1996). A possible explanation for the reduced severity of the defects as compared to those in the progeny of drug-treated rats is cholesterol supplementation from heterozygous mothers via placental exchange. Consistent with this idea, high dietary cholesterol can suppress the teratogenic effects of cholesterol synthesis inhibitors given to pregnant rats (Roux et al. 1979) Some of the developmental malformations in SLOS patients are likely to result from deficiencies in steroid hormone biosynthesis as well as from effects on other unknown targets.

Related developmental defects have also been described in mouse mutants lacking function of the endocytic receptor megalin or apolipoprotein B (Herz et al. 1997). The megalin protein, also referred to as gp330, is encoded by a member of the low density lipoprotein (LDL) receptor gene family and is specifically expressed on the apical surfaces of embryonic neuroectoderm and neuroepithelium in the developing neural tube. Apolipoprotein B (apoB) is the major structural component of several lipoprotein particles that carry esterified cholesterol and other neutral lipids in the circulation. The defects in megalin-deficient mice include fusion of forebrain structures into a single vesicle, agenesis of the olfactory bulbs and pituitary, and absence of the corpus callosum, all malformations within the holoprosencephaly sequence and therefore suggestive of a perturbation in the Shh signaling pathway (Willnow et al. 1996). The defects in mice lacking apoB function are more severe, appear less specific and cause resorption of most homozygous embryos by 9.5 or 10.5 days of gestation (Farese et al. 1995; Huang et al. 1995). Mutations in both of these genes affect cholesterol transport, with the difference that the megalin effect may be restricted to cholesterol uptake in neural precursors whereas the apoB defect would block all embryonic absorption of maternally derived cholesterol, normally transported via the yolk sac in the mouse (Farese et al. 1996). A hypomorphic mutation that produces a truncated but functional apoB protein is homozygous viable and does not consistently show developmental defects (Homanics et al. 1993). The reduced cholesterol levels in these mice, however, makes them susceptible to teratogenesis with the compound BM 15.766 and the resulting defects, including holoprosencephaly, are like those in treated rats (Lanoue et al 1997). Normal mice are not susceptible to treatments with cholesterol synthesis inhibitors, possibly because their cholesterol levels are higher than those in rats.

Plant Teratogens as Cholesterol Synthesis Inhibitors

Another experimental model for holoprosencephaly derives from the occurrence of epidemics of congenital craniofacial malformations among newborn lambs on sheep ranches in several National Forests of the western United States (Gaffield and Keeler 1996). The most dramatically affected lambs showed severe holoprosencephaly, including true cyclopia and other craniofacial malformations characteristic of holoprosencephaly. The occurrence of these defects was traced to grazing by pregnant ewes on the range plant *Veratrum californicum* (Binns et al. 1963). The compounds responsible were identified by Keeler and Binns (1968) as a family of steroidal alkaloids; the structures of two of these, cyclopamine and jervine, are shown as compared to cholesterol in FIG. 6A.

Figure 5:
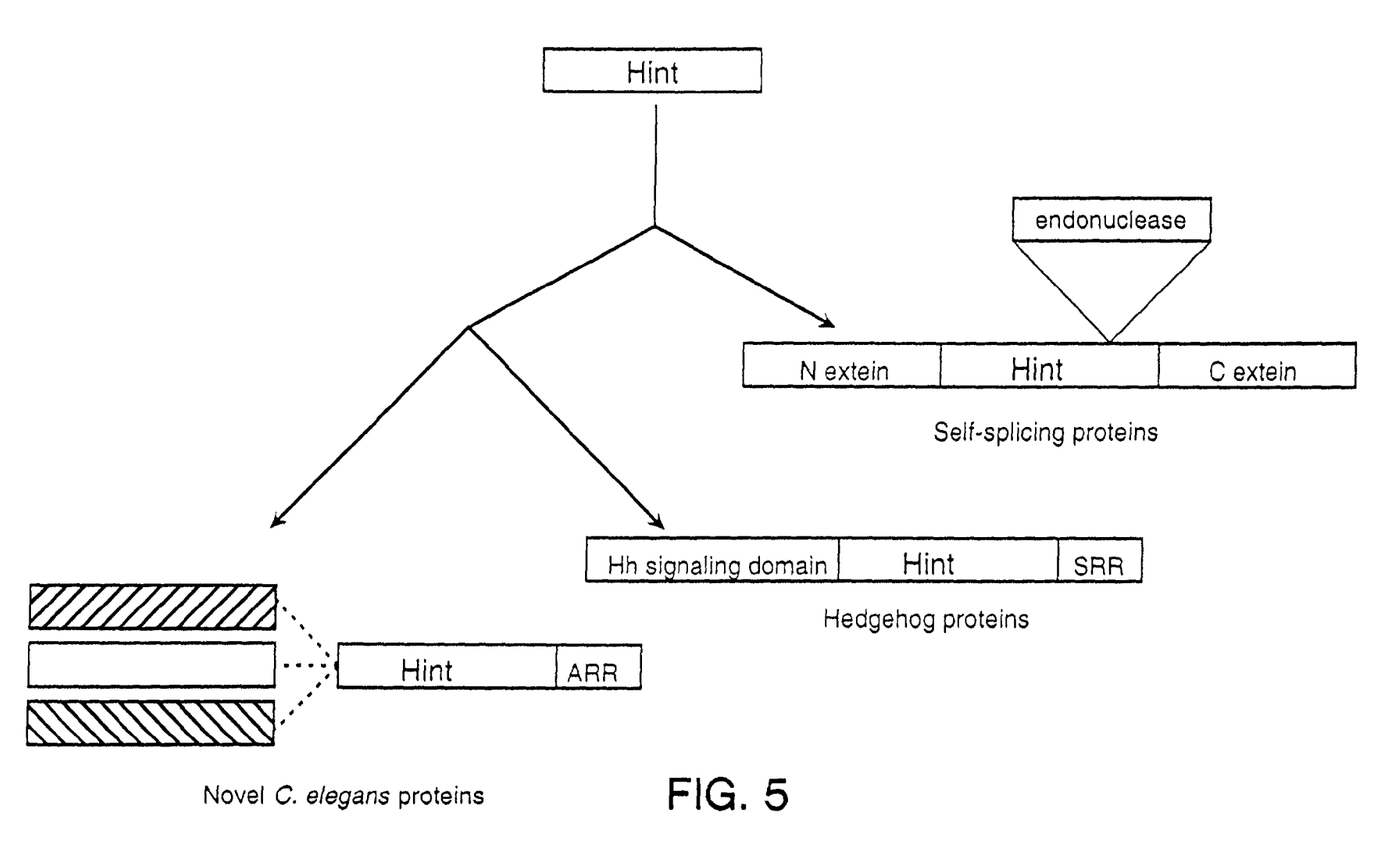

Given the structural similarities of these compounds to cholesterol and the similar teratogenic effects of cholesterol synthesis inhibitors upon the offspring of pregnant rats, a reasonable mechanism to consider for the effects of these plant sterol derivatives was the inhibition of cholesterol biosynthesis. Accordingly, we tested COS7 cultured cells treated with jervine for defects in cholesterol biosynthesis by labelling with [3H]-mevalonic acid and then extracting and analyzing radiolabelled, non-saponifiable lipids. FIG. 5B shows that treated cells synthesized reduced levels of cholesterol and accumulated increased levels of another sterol that we have provisionally identified as the cholesterol precursor, zymosterol. The natural product jervine at these concentrations thus inhibits cholesterol biosynthesis in cultured cells in much the same manner as the synthetic drugs discussed above, although the specific enzyme(s) affected appear to differ. Given the similarities in their teratogenic effects, this inhibition seems likely to underlie the teratogenic effects of both the synthetic and natural compounds.

Perturbations of Cholesterol Homeostasis Block the Response to Shh Signaling

As reviewed above, there is a striking correspondence between the developmental malformations in mouse and human Shh mutants and those caused by perturbations of cholesterol homeostasis. These malformations are caused by effects on either synthesis or transport of cholesterol; in the case of the hypomorphic apob allele combined with BM 15.766 treatment, effects on both synthesis and transport appear to synergize in generating severe holoprosencephaly in mice, where neither effect alone suffices (Lanoue et al. 1997). The developmental malformations caused by these perturbations of cholesterol homeostasis strongly suggest that the Shh signaling pathway or its targets must somehow be affected. Our attention initially was drawn to these perturbations because of the role of cholesterol in Hh autoprocessing and the possibility that autoprocessing and hence signal production might be affected. But a second possibility is that instead of an effect on signal production these perturbations of cholesterol homeostasis might interfere with the ability of target tissues to sense or transduce the Shh signal. To distinguish these two possibilities we have examined the effects of these synthetic and plant-derived compounds on the autoprocessing reaction in vivo and in vitro, and have also tested the ability of drug-treated neural plate explants to respond to recombinant Shh protein.

The autoprocessing reaction is not inhibited by these compounds in cultured cells, nor is cleavage and cholesterol modification inhibited in the in vitro reaction (M.K.C., J.A.P., K.E.Y, P.A.B., manuscript in preparation). The amino-terminal product of processing in drug-treated cultured cells displays a mobility suggestive of sterol modification. Since a number of cholesterol biosynthetic precursors are able to participate in the in vitro reaction, the adduct could either be cholesterol or one of the precursors whose accumulation is caused by drug treatment. The lack of any apparent effect on processing leaves open the second possibility, that drug treatment affects the ability of target tissues to respond to the Shh signal. This possibility is supported by our observations with neural plate explants, in which target genes normally induced by recombinant Shh-N protein are unresponsive when the explants are treated with synthetic and plant-derived cholesterol synthesis inhibitors (M.K.C., J.A.P., K.E.Y, P.A.B., manuscript in preparation). An effect on target tissues also is consistent with the occurrence of HPE in megalin mutant mice and with the specific expression of megalin in embryonic neuroepithelium during the critical period of Shh signaling (Willnow et al. 1996). The megalin receptor is able to mediate LDL uptake (Stefansson et al. 1995), and no developmental defects are observed in mice or humans lacking function of the more generally expressed LDL receptor (Ishibashi et al. 1993). This suggests that megalin may function specifically to maintain cholesterol homeostasis in developing neuroepithelium, which is the target of Shh protein signaling during the HPE critical period. A link between cholesterol homeostasis and activity of the Hh pathway is interesting since most responses to Hh signaling in neuroepithelium or other developing tissues involve cell proliferation. This linkage might make sense from a regulatory point of view, given the importance of cholesterol as a membrane component in dividing cells.

Additional information consistent with a role for cholesterol in receiving the Shh signal derives from the recent isolation of the Niemann-Pick C (NP-C) disease gene from mouse and human (Carstea et al. 1997; Loftus et al. 1997). The NP-C protein contains 13-16 transmembrane domains, and two features of its sequence are notable in the context of Shh signaling (Carstea et al. 1997; Loftus et al. 1997). The first is that it resembles that of the Hh pathway protein Patched (Ptc) throughout most of its extent, and the second is that five of the NP-C transmembrane domains constitute an apparent sterol sensing domain (SSD), which had not previously been noticed in Ptc.

SSD sequences are also present in HMG-CoA reductase and SCAP (SREBP cleavage activating protein; Hua et al. 1996), two proteins involved in maintenance of cholesterol homeostasis (FIG. 6). Although it is not yet known whether the SSD binds cholesterol directly or instead indirectly senses cholesterol-induced changes in membrane properties (see e.g., Nezil and Bloom 1992), the SSD in these proteins is required for a response to distinct levels of cellular cholesterol. In the case of HMG-CoA reductase, the rate-limiting enzyme in the cholesterol biosynthetic pathway, the SSD mediates decreased enzyme stability under conditions of cholesterol excess (Gil et al. 1985). The SCAP protein responds to sterol levels by modulating the cleavage and activation of SREBP (sterol response element binding protein), a transcription factor that controls expression of proteins involved in cholesterol synthesis and uptake (Brown and Goldstein 1997); in the absence of cleavage SREBP remains anchored to the endoplasmic reticulum via two transmembrane domains. The NP-C protein itself appears to play a role in cholesterol homeostasis by directly acting in or by regulating cholesterol transport, as indicated in NP-C cultured cells by a delayed response to challenge by LDL with a consequent accumulation of cholesterol in lysosomes.

The Ptc protein has been suggested to constitute or contribute to the Hh receptor mechanism, but its role is not that of a conventional receptor. In the absence of Ptc function the Hh signaling pathway is constitutively activated (Ingham et al. 1991). The normal function of Ptc thus seems to be suppression of the pathway in target cells, and this suppression is alleviated by the presence of the Hh signal. In addition to this cell autonomous role in suppressing the pathway, the Ptc protein has a role in sequestration of the Hh signal within tissues, a non-cell autonomous activity which affects the spatial extent of Hh signaling (Chen and Struhl 1996). These two activities can be genetically uncoupled, as demonstrated by a mutant protein that retains the sequestration function but, like other Ptc mutations, does not suppress the Hh pathway (Chen and Struhl 1996). Recent biochemical evidence suggests that Shh-N protein may interact directly with the mouse Ptc protein, (Marigo et al. 1996; Stone et al. 1996) but, assuming that a direct interaction can be confirmed with the use of purified components, it is unclear whether it would play a role in either, both, or neither of the Ptc functions described above.

These biochemical experiments were carried out with recombinant protein that lacked the cholesterol modification (Marigo et al. 1996; Stone et al. 1996). In light of the presence of an SSD within Ptc, it would be interesting to know whether the Hh cholesterol adduct influences the apparent affinity of the amino-terminal signaling domain for Ptc. Along these lines it is interesting to note that *Drosophila* embryos expressing a truncated hh construct in the normal spatial pattern (Porter et al. 1996a) are similar to embryos that ectopically express full-length Hh and to embryos that lack Ptc function (Chang et al. 1994; Ingham 1993; Porter et al. 1996a): all three of these genotypes show spatially indiscriminate activation of the Hh pathway. One possible explanation of these similarities is that the cholesterol adduct not only increases the association of Hh signaling domain with producing cells but also contributes favorably to the interaction with Ptc. In the absence of the cholesterol adduct, the Hh-N protein would not be as effectively sequestered by Ptc, leading to ectopic Hh pathway activation.

An enhanced sequestration by Ptc of the cholesterol-modified signaling domain would represent a role distinct from that of mediating the response to cholesterol homeostasis within the target cell, although it is conceivable that the Ptc SSD might be involved in both. Given our incomplete knowledge of the mechanistic role of Ptc, all discussion as to the role of its SSD must be considered speculative. But the presence of a SSD in a protein with such a central role in regulating the Hh response is tantalizing as the possible link to the dual roles of cholesterol in limiting the spatial extent of Hh signaling and in facilitating transduction of the Hh signal within target cells.

Figures 6A, 6B:
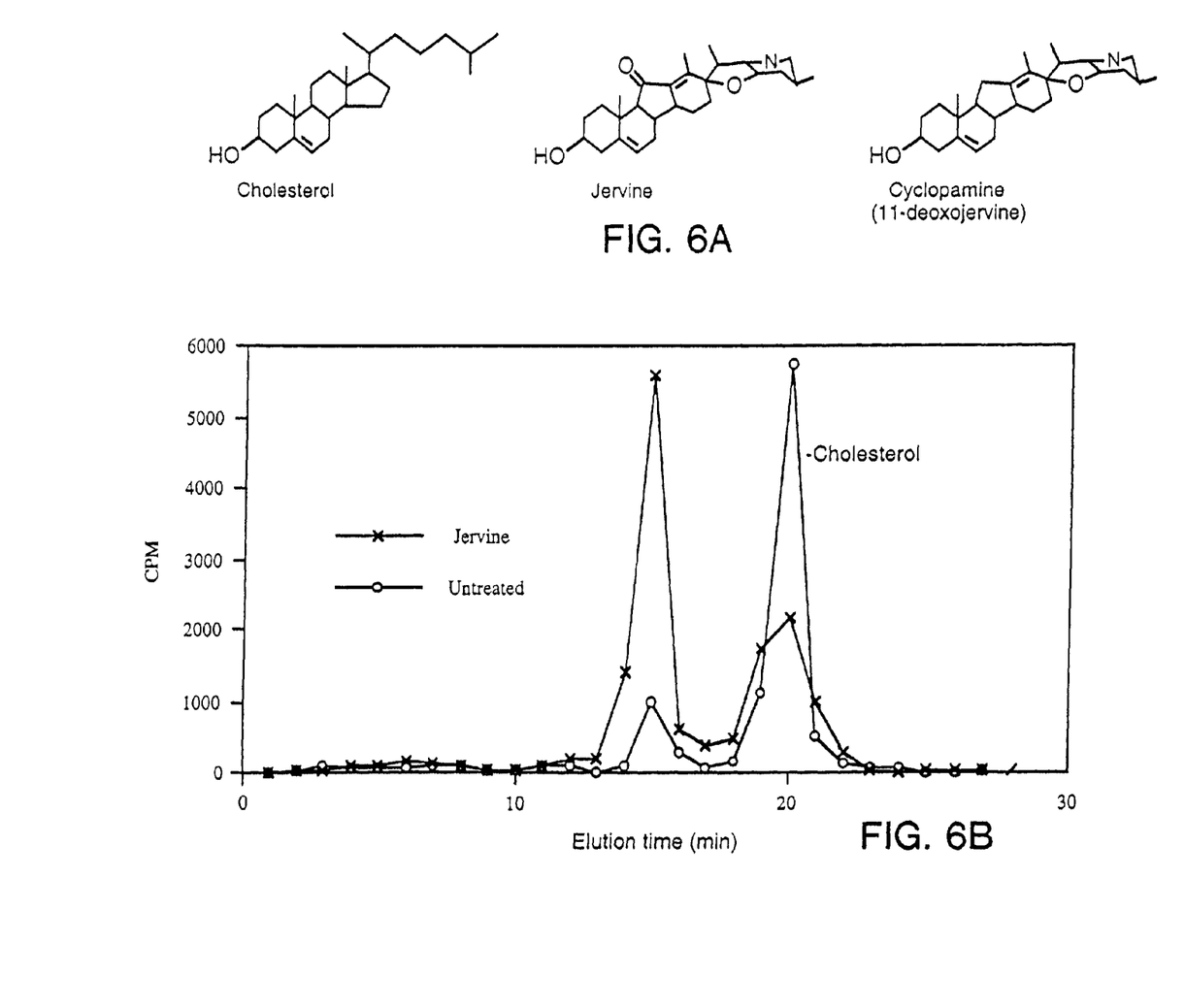
Figure 7:
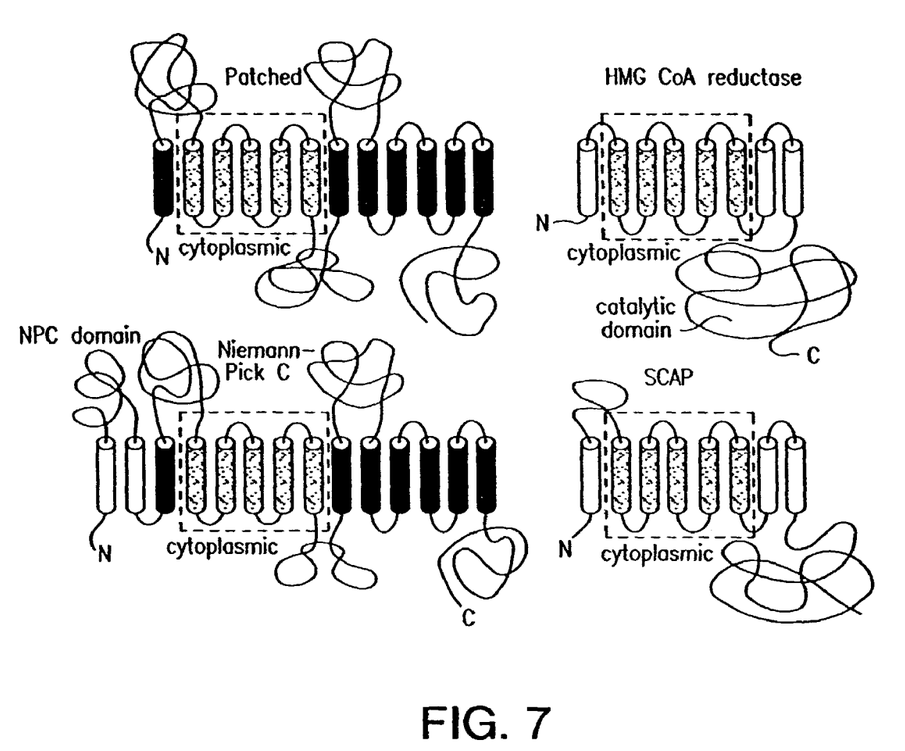

An experimental model for holoprosencephaly derives from the occurrence of epidemics of congenital craniofacial malformations among newborn lambs on sheep ranches in several National Forests of the western United States. The most dramatically affected lambs showed severe holoprosencephaly, including true cyclopia and other craniofacial malformations characteristic of holoprosencephaly. The occurrence of these defects was traced to grazing by pregnant ewes on the range plant *Veratrum californicum*. The compounds responsible were identified as a family of steroidal alkaloids; the structures of two of these, cyclopamine and jervine, are shown as compared to cholesterol in FIG. 6B. In FIG. 6B, sterols were extracted and analyzed by HPLC from COST cells metabolically labelled with [$^3$H]-mevalonic acid in the presence or absence of jervine, a teratogenic plant steroidal alkaloid. In the presence of 28 mM jervine, radiolabelled cholesterol levels were reduced and another radiolabelled sterol was found to accumulate. On the basis of its retention time in this reverse phase HPLC method, this abnormal sterol is tentatively identified as zymosterol, an intermediate in the cholesterol biosynthetic pathway.

Given the structural similarities of these compounds to cholesterol and the similar teratogenic effects of cholesterol synthesis inhibitors upon the offspring of pregnant rats, a reasonable mechanism to consider for the effects of these plant sterol derivatives was the inhibition of cholesterol biosynthesis. Accordingly, COS7 cultured cells treated with jervine were tested for defects in cholesterol biosynthesis by labelling with [3H]-mevalonic acid and then extracting and analyzing radiolabelled, non-saponifiable lipids.

Metabolic labeling and sterol analysis was essentially as described (Popjak et al. *J. Biol. Chem.* 264: 630-6238.1989; Rilling et al. 1993 *Arch. Biochem. Biophys.* 301: 210-215.), with minor modifications. Briefly, COS-7 cells were plated at ~35% confluence into two 60 mm dishes at 37° C. in 4 ml each of Dulbecco's modified Eagle's medium (DMEM) supplemented with 10% fetal bovine serum (FBS). After 24 hr of growth the medium in each dish was replaced with 2 ml fresh medium with 10% FBS; [$^3$H]-mevalonic acid (NEN #NET 176) brought to a specific activity of 0.8 Ci/mmol in a 1% solution of bovine serum albumin was added to this medium to a final concentration of 20 mM. At this time, one dish received 6 ml of a 4 mg/ml solution of jervine in ethanol (final concentration 28 mM jervine), and the other received 6 ml of ethanol. After 24 hr further incubation, cells were washed in PBS, extracted with methanol, and 1 M potassium hydroxide (KOH) added to 10%. Following a three hour incubation at 60° C., the methanol/KOH mixture was extracted with diethyl ether, the extract dried down, resuspended in isopropanol, and subjected to reverse phase HPLC analysis by the method of Rodriguez and Parks (*Methods in Enzymology* 111: 37-511985).

Treated cells synthesized reduced levels of cholesterol and accumulated increased levels of another sterol that we have provisionally identified as the cholesterol precursor, zymosterol. The natural product jervine at these concentrations thus inhibits cholesterol biosynthesis in cultured cells in much the same manner as the synthetic drugs discussed above, although the specific enzyme(s) affected appear to differ. Given the similarities in their teratogenic effects, this inhibition seems likely to underlie the teratogenic effects of both the synthetic and natural compounds.

EXAMPLES

Immunostaining and Blotting of Hh Protein

For immunostaining, stably transfected Schneider line 2 (S2) cultured cells harboring full-length Hh under metallothionein promoter control (Porter et al 1995) were induced by adding CuSO4 (0.5 mM) to the medium, incubated overnight, transferred to an 8-chamber slide (Nunc) and allowed to adhere for one hour. The cells were fixed with 4% paraformaldehyde/PBS for 10 min at room temperature (RT) and washed several times with PBSS (PBS containing 0.1% saponin). The cells were as follows, several PBSS washes at every reagent change: anti-N (1:100 dilution of anti Hh-N described in Lee et al 1994) for one hour, anti-rabbit-Texas Red (1:50 dilution, Jackson ImmunoResearch Laboratories) for 30 min. All incubations were performed at RT and the antibodies were diluted in 1% BSA/PBSS. The cells were mounted with Vectashield (Vector Laboratories) and observed by confocal microscopy (Biorad).

For immunoblotting, medium and cells from cultures of stably transfected S2 cells expressing full-length or truncated Hh were suspended in SDS sample buffer, and equivalent fractions of the total culture were loaded onto a 12% polyacrylamide gel, electrophoresed and transferred to nitrocellulose Amino-terminal epitopes were detected with anti-Hh-N antibody (Lee et al. 1994) and bound antibody was detected with ECL (Amersham).

Jervine Inhibition of Cholesterol Biosynthesis

Metabolic labeling and sterol analysis was essentially as described (Popjak et al. 1989; Rilling et al. 1993; Rodriguez and Parks 1985), with minor modifications. Briefly, COS-7 cells were plated at ~35% confluence into two 60 mm dishes at 37° C. in 4 ml each of Dulbecco's modified Eagle's medium (DMEM) supplemented with 10% fetal bovine serum (FBS). After 24 hr of growth the medium in each dish was replaced with 2 ml fresh medium with 10% FBS; [3H]-mevalonic acid (NEN #NET 176) brought to a specific activity of 0.8 Ci/mmol in a 1% solution of bovine serum albumin was added to this medium to a final concentration of 20=|M. At this time, one dish received 6=|1 of a 4 mg/ml solution of jervine in ethanol (final concentration 28=|M jervine), and the other received 6=|1 of ethanol. After 24 hr further incubation, cells were washed in PBS, extracted with methanol, and 1 M potassium hydroxide (KOH) added to 10%. Following a three hour incubation at 60✓ C, the methanol/KOH mixture was extracted with diethyl ether, the extract dried down, resuspended in isopropanol, and subjected to reverse phase HPLC analysis by the method of Rodriguez and Parks (1985).

REFERENCES

Adelmann, H. B. 1936b. The problem of cyclopia. Quart. Rev. Biol. 11: 284-304.

Adelmann, H. B. 1936a. The problem of cyclopia. Quart. Rev. Biol. 11: 116-182.

Belloni, E., Muenke, M., Roessler, E., Traverso, G., Siegel-Bartelt, J., Frumkin, A., Mitchell, H. F., Donis-Keller, H., Helms, C., Hing, A. V., Heng, H. H. Q., Koop, B., Martindale, D., Rommens, J. M., Tsui, L.-C., and Scherer, S. W. 1996. Identification of Sonic hedgehog as a candidate gene responsible for holoprosencephaly Nature Genet. 14: 353-356.

Binns, W., James, L. F., Shupe, J. L., and Everett, G. 1963. A congenital cyclopian-type malformation in lambs induced by maternal ingestion of a range plant, Veratrum californicum. Am. J. Vet. Res. 24: 1164-1175.

Brannigan, J. A., Dodson, G., Duggleby, H. J., Moody, P. C. E., Smith, J. L., Tomchick, D. R., and Murzin, A. G. 1995. A protein catalytic framework with an N-terminal nucleophile is capable of self-activation. Nature 378: 416-419.

Brown, M. S., and Goldstein, J. L. 1997. The SREBP pathway: Regulation of cholesterol metabolism by proteolysis of a membrane-bound transcription factor. Cell 89: 331-340.

Bumcrot, D. A., Takada, R., and McMahon, A. P. 1995. Proteolytic processing yields two secreted forms of Sonic hedgehog. Mol. Cell. Biol. 15: 2294-2303.

Burglin, T. R. 1996. Warthog and Groundhog, novel families related to Hedgehog. Curr. Biol. 6: 1047-1050.

Carstea, E. D., Morris, J. A., Coleman, K. G., Loftus, S. K., Zhang, D., Cummings, C., Gu, J., Rosenfeld, M. A., Pavan, W. J., Krizman, D. B., Nagle, J., Polymeropoulos, M. H., Sturley, S. L., Ioannou, Y. A., Higgins, M. E., Comly, M., Cooney, A., Brown, A., Kaneski, C. R., Blanchette-Mackie, E. J., Dwyer, N. K., Neufeld, E. B., Chang, T.-Y, Liscum, L., Strauss III, J. F., Ohno, K., Zeigler, M., Carmi, R., Sokol, J., Markie, D., O'Neill, R. R., van Diggelen, O. P., Elleder, M., Patterson, M. C., Brady, R. O., Vanier, M. T., Pentchev, P. G., and Tagle, D. A. 1997. Niemann-Pick C1 disease gene: Homology to mediators of cholesterol homeostasis. Science 277: 228-231.

Chang, D. T., Lopez, A., von Kessler, D. P., Chiang, C., Simandl, B. K., Zhao, R., Seldin, M. E, Fallon, J. F., and Beachy, P. A. 1994. Products, genetic linkage, and limb patterning activity of a murine hedgehog gene. Development 120: 3339-3353.

Chen, Y., and Struhl, G. 1996. Dual roles for patched in sequestering and transducing hedgehog. Cell 87: 553-563.

Chiang, C., Litingtung, Y., Lee, E., Young, K., Corden, J. L., Westphal, H., and Beachy, P. 1996. Cyclopia and defective axial patterning in mice lacking Sonic hedeghog gene function. Nature 383: 407-413.

Chu, C. T., and Pizzo, S. V. 1994. Alpha-2 macroglobulin, complement, and biological defense: antigens, growth factors, microbial proteases, and receptor ligation. Laboratory Investigation 71: 792-812.

Cohen, M. M., and Sulilk, K. K. 1992. Perspectives on holoprosencephaly: Part II. Central nervous system, craniofacial anatomy, syndrome commentary, diagnostic approach, and experimental studies. J. Craniofac. Genet. Dev. Biol. 12: 196-244.

Dalgaard, J. Z., Moser; M. J., Hughey, R., and Mian, I. S. 1997. Statistical modeling, phylogenetic analysis and structure prediction of a protein splicing domain common to inteins and Hedgehog proteins. J. Comput. Biol. 4: 193-214.

Dawson, P. E., Muir, T. W., Clark-Lewis, I., and Kent, S. B. H. 1994. Synthesis of proteins by native chemical ligation. Science 266: 776-779.

Dehart, D. B., Lanoue, L., Tint, G. S., and Sulik, K. K. 1997. Pathogenesis of malformations in a rodent model for Smith-Lemli-Opitz Syndrome. Am. J. Med. Genet. 68: 328-337.

Dideberg, O., Charlier, P., Dive, G., Joris, B., FrÄre, J. M., and Ghuysen, J. M. 1982. Structure of a Zn2+-containing D-alanyl-D-alanine-cleaving carboxypeptidase at 2.5 ü resolution. Nature 299: 469-470.

Duan, X., Gimble, F. S., and Quiocho, F. A. 1997. Crystal structure of PI-SceI, a homing endonuclease with protein splicing activity. Cell 89: 555-564.

Echelard, Y., Epstein, D. J., St-Jacques, B., Shen, L., Mohler, J., McMahon, J. A., and McMahon, A. P. 1993. Sonic hedgehog, a member of a family of putative signalling molecules, is implicated in the regulation of CNS polarity Cell 75: 1417-1430.

Ekker, S.C., Ungar, A. R., Greenstein, P., von Kessler, D. P., Porter, J. A., Moon, R. T., and Beachy, P. A. 1995. Patterning activities of vertebrate hedgehog proteins in the developing eye and brain. Current Biology 5: 944-955.

Ericson, J., Rashbass, P., Schedl, A., Brenner-Morton, S., Kawakami, A., van Heyningen, V., Jessell, T. M., and Briscoe, J. 1997. Pax6 controls progenitor cell identity and neuronal fate in response to graded Shh signaling. Cell 90: 169-180.

Farese, R. V., Cases, S., Ruland, S. L., Kayden, H. J., Wong, J. S., Young, S. G., and Hamilton, R. L. 1996. A novel function for apolipoprotein B: lipoprotein synthesis in the yolk sac is critical for maternal-fetal lipid transport in mice. J. Lipid Res. 37: 347-360.

Farese, R. V., Ruland, S. L., Flynn, L. M., Stokowski, R. P., and Young, S. G. 1995. Knockout of the mouse apolipoprotein B gene results in embryonic lethality in homozygotes and protection against diet-induced hypercholesterolemia in heterozygotes. Proc. Natl. Acad. Sci. U.S.A. 92: 1774-1778.

Gaffield, W., and Keeler, R. F. 1996. Steroidal alkaloid teratogens: Molecular probes for investigation of craniofacial malformations. J. Toxicology 15: In press.

Gil, G., Faust, J. R., Chin, D. J., Goldstein, J. L., and Brown, M. S. 1985. Membrane-bound domain of HMG CoA reductase is required for sterol-enhanced degradation of the enzyme. Cell 41: 249-258.

Goodrich, L. V., Johnson, R. L., Milenkovic, L., McMahon, J. A., and Scott, M. P. 1996. Conservation of the hedgehog/patched signaling pathway from flies to mice: induction of a mouse patched gene by Hedgehog. Genes & Dev. 10: 301-312.

Guan, C., Cui, T., Rao, V., Liao, W., Benner, J., Lin, C.-L., and Comb, D. 1996. Activation of glycosylasparaginase: Formation of active N-terminal threonine by intramolecular autoproteolysis. J. Biol. Chem. 271: 1732-1737.

Hall, T. M. T., Porter, J. A., Beachy, P. B., and Leahy, D. J. 1995. A potential catalytic site revealed by the 1.7-ë crystal structure of the amino-terminal signalling domain of Sonic hedgehog. Nature 378: 212-216.

Hall, T. M. T., Porter, J. A., Young, K. E., Koonin, E. V., Beachy, P. A., and Leahy, D. J. 1997. Crystal structure of a Hedgehog autoprocessing domain: Conservation of structure, sequence, and reaction mechanism between Hedgehog and self-splicing proteins. Cell, in press.

Hammerschmidt, M., Brook, A., and McMahon, A. P. 1997. The world according to hedgehog. Trends Genet. 13: 14-21.

Herz, J., Willnow, T. E., and Farese Jr., R. V. 1997. Cholesterol, hedgehog and embryogenesis. Nature Genet. 15: 123-124.

Hochstrasser, M. 1996. Ubiquitin-dependent protein degradation. Annu. Rev. Genet. 30: 405-439.

Homanics, G. E., Smith, T. J., Zhang, S. H., Lee, D., Young, S. G., and Maeda, N. 1993. Targeted modification of the apolipoprotein B gene results in hypobetalipoproteinemia and developmental abnormalities in mice. Proc. Natl. Acad. Sci. U.S.A. 90: 2389-2393.

Hua, X., Nohturfft, A., Goldstein, J. L., and Brown, M. S. 1996. Sterol resistance in CHO cells traced to point mutation in SREBP cleavage-activating protein. Cell 87: 415-426.

Huang, L.-S., Voyiaziakis, E., Markenson, D. F., Sokol, K. A., Hayek, T., and Breslow, J. L. 1995. apo B gene knockout in mice results in embryonic lethality in homozygotes and neural tube defects, male infertility, and reduced HDL cholesterol ester and apo A-1 transport rates in heterozygotes. J. Clin. Invest. 96: 2152-2161.

Ingham, P. W. 1993. Localized hedgehog activity controls spatial limits of wingless transcription in the *Drosophila* embryo. Nature 366: 560-562.

Ingham, P. W., Taylor, A. M., and Nakano, Y. 1991. Role of the *Drosophila* patched gene in positional signalling. Nature 353: 184-187.

Ishibashi, S., Brown, M. S., Goldstein, J. L., Gerard, R. D., Hammer, R. E., and Herz, J. 1993. Hypercholesterolemia in low density lipoprotein receptor knockout mice and its reversal by adenovirus-mediated gene delivery. J. Clin. Invest. 92: 883-893.

Keeler, R. F., and Binns, W. 1968. Teratogenic compounds of *Veratrum californicum* (Durand): V. Comparison of cyclopian effects of steroidal alkaloids from the plant and structurally related compounds from other sources. Teratology 1: 5-10.

Kelley, R. I., Roessler, E., Hennekam, R. C. M., Feldman, G. I., Kosaki, K., Jones, M. C., Palumbos, J. C., and Muenke, M. 1996. Holoprosencephaly in RSH/Smith-Lemli-Opitz Syndrome: Does abnormal cholesterol metabolism affect the function of Sonic Hedgehog. Am. J. of Med. Gen. 66: 478-484.

Lai, C.-J., Ekker, S. C., Beachy, P. A., and Moon, R. T. 1995. Patterning of the neural ectoderm of *Xenopus laevis* by the amino-terminal product of hedgehog autoproteolytic cleavage. Development 121: 2349-2360.

Lanoue, L., Dehart, D. B., Hinsdale, M. E., Maeda, N., Tint, G. T., and Sulik, K. K. 1997. Limb, genital, CNS and facial malformations result from gene/environment-induced cholesterol deficiency: Further evidence for a link to Sonic Hedgehog. Am. J. Med. Genet. in press.

Lee, J. J., Ekker, S.C., von Kessler, D. P., Porter, J. A., Sun, B. I., and Beachy, P. A. 1994. Autoproteolysis in hedgehog protein biogenesis. Science 266: 1528-1537.

Lee, J. J., von Kessler, D. P., Parks, S., and Beachy, P. A. 1992. Secretion and localized transcription suggest a role in positional signaling for products of the segmentation gene hedgehog. Cell 71: 33-50.

Loftus, S. K., Morris, J. A., Carstea, E. D., Gu, J. Z., Cummings, C., Brown, A., Ellison, J., Ohno, K., Rosenfeld, M. A., Tagle, D. A., Pentchev, P. G., and Pavan, W. J. 1997. Murine model of Niemann-Pick C diesease: Mutation in a cholesterol homeostasis gene. Science 277: 232-235.

Mangold, O. 1931. Das determinationsproblem. III. Das wirbeltierauge in der entwicklung und regeneration. Ergeb. d. Biol. 7: 193-403.

Marigo, V., Davey, R. A., Zuo, Y., Cunningham, J. M., and Tabin, C. J. 1996. Biochemical evidence that Patched is the Hedgehog receptor. Nature 384: 176-179.

Marti, E., Bumcrot, D. A., Takada, R., and McMahon, A. P. 1995. Requirement of 19K form of sonic hedgehog for induction of distinct ventral cell types in CNS explants. Nature 375: 322-325.

Mohler, J. 1988. Requirements for hedgehog, a segmental polarity gene, in patterning larval and adult cuticle of *Drosophila*. Genetics 120: 1061-1072.

Mohler, J., and Vani, K. 1992. Molecular organization and embryonic expression of the hedgehog gene involved in cell-cell communication in segmental patterning of *Drosophila*. Development 115: 957-971.

Murzin, A. G. 1996. Structural classification of proteins: new superfamilies. Curr. Opin. Struct. Biol. 6: 386-394.

Nezil, F. A., and Bloom, M. 1992. Combined influence of cholesterol and synthetic amphiphilic peptides upon bilayer thickness in model membranes. Biophys. J. 61: 1176-1183.

Olender, E. H., and Simoni, R. D. 1992. The intracellular targeting and membrane topology of 3-hydroxy-3-methyl-glutaryl-CoA reductase. J. Biol. Chem. 267: 4223-4235.

Opitz, J. M. 1994. RSH/SLO ("Smith-Lemli-Opitz") syndrome: historical, genetic, and developmental considerations. American Journal of Medical Genetics 50: 344-346.

Perler, F. B., Davis, E. O., E., D. G., Gimble, F. S., Jack, W. E., Neff, N., Noren, C. J., Thorner, J., and Belfort, M. 1994. Protein splicing elements: inteins and exteins—a definition of terms and recommended nomenclature. Nucleic Acids Res. 22: 1125-1127.

Pietrokovski, S. 1997. Modular organization of inteins and C-terminal autocatalytic domains. Prot. Sci., in press.

Placzek, M., Jessell, T. M., and Dodd, J. 1993. Induction of floor plate differentiation by contact-dependent, homeogenetic signals. Development 117: 205-218.

Popjak, G., Meenan, A., Parish, E. J., and Nes, W. D. 1989. Inhibition of cholesterol synthesis and cell growth by 24(R, S), 25-iminolanosterol and triparanol in cultured rat hepatoma cells. J. Biol. Chem. 264: 630-6238.

Porter, J. A., Ekker, S.C., Park, W.-J., von Kessler, D. P., Young, K. E., Chen, C.-H., Ma, Y., Woods, A. S., Cotter, R. J., Koonin, E. V., and Beachy, P. A. 1996a. Hedgehog patterning activity: Role of a lipophilic modification mediated by the carboxy-terminal autoprocessing domain. Cell 86: 21-34.

Porter, J. A., von Kessler, D. P., Ekker, S.C., Young, K. E., Lee, J. J., Moses, K., and Beachy, P. A. 1995. The product of hedgehog autoproteolytic cleavage active in local and long-range signalling. Nature 374: 363-366.

Porter, J. A., Young, K. E., and Beachy, P. A. 1996b. Cholesterol modification of Hedgehog signaling proteins in animal development. Science 274: 255-259.

Rilling, H. S., Bruenger, E., Leining, L. M., Buss, J. E., and Epstein, W. W. 1993. Differential prenylation of proteins as a function of mevalonate concentration in CHO cells. Arch. Biochem. Biophys. 301: 210-215.

Rodriguez, R. J., and Parks, L. W. 1985. High-performance liquid chromatography of sterols: yeast sterols. Methods in Enzymology III: 37-51.

Roelink, H., Porter, J. A., Chiang, C., Tanabe, Y., Chang, D. T., Beachy, P. A., and Jessell, T. M. 1995. Floor plate and motor neuron induction by different concentrations of the amino-terminal cleavage product of Sonic hedgehog autoproteolysis. Cell 81: 445-455.

Roessler, E., Belloni, E., Gaudenz, K., Jay, P., Berta, P., Scherer, S. W., Tsui, L.-C., and Muenke, M. 1996. Mutations in Sonic hedgehog gene cause holoprosencephaly. Nature Genet. 14: 357-360.

Roitelman, J., Olender, E. H., Bar-Nun, S., Dunn Jr., W. A., and Simoni, R. D. 1992. Immunological evidence for eight spans in the membrane domain of 3-hydroxy-3-methylglutaryl coenzyme A reductase: Implications for gene degradation in the endoplasmic reticulum. J. Cell Biol. 117: 959-973.

Roux, C. 1966. Action teratogene chez le rat d'un inhibiteur de la synthese du cholesterol, le AY9944. C. R. Soc. Biol. 160: 1353-1357.

Roux, C. 1964. Action teratogene du triparanol chez l'animal. Arch. franc. Pediatr. 21: 451-464.

Roux, C., Horvath, C., and Dupuis, R. 1979. Teratogenic action and embryo lethality of AY 9944R: Prevention by a hypercholesterolemia-provoking diet. Teratology 19: 35-38.

Salen, G., Shefer, S., Batta, A. K., Tint, G. S., Xu, G., Honda, A., Irons, M., and Elias, F. R. 1996. Abnormal cholesterol biosynthesis in the Smith-Lemli-Opitz syndrome. J. Lipid Res. 37: 1169-1180.

Stefansson, S., Chappell, D. A., Argraves, K. M., Strickland, D. K., and Argraves, W. S. 1995. Glycoprotein 330/low density lipoprotein receptor-related protein-2 mediates endocytosis of low density lipoproteins via interaction with apolipoprotein B100. J. Biol. Chem. 270: 19417-19421.

Stone, D. M., Hynes, M., Armanini, M., Swanson, T. A., Gu, Q., L., J. R., Scott, M. P., Pennica, D., Goddard, A., Phillips, H., Noll, M., Hooper, J. E., de Sauvage, F., and Rosenthal, A. 1996. The tumor-suppressor gene patched encodes a candidate receptor for Sonic hedgehog. Nature 384: 129-134.

Tabata, T., Eaton, S., and Kornberg, T. B. 1992. The *Drosophila* hedgehog gene is expressed specifically in posterior compartment cells and is a target of engrailed regulation. Genes and Development 6: 2635-2645.

Tashiro, S., Michiue, T., Higashijima, S., Zenno, S., Ishimaru, S., Takahashi, F., Orihara, M., Kojima, T., and Saigo, K. 1993. Structure and expression of hedgehog, a *Drosophila* segment-polarity gene required for cell-cell communucation. Gene 124: 183-189.

Tint, G. S., Irons, M., Elias, E. R., Batta, A. K., Frieden, R., Chen, T. S., and Salen, G. 1994. Defective cholesterol biosynthesis associated with the Smith-Lemli-Opitz syndrome. New England Journal of Medicine 330: 107-113.

van Poelje, P. D., and Snell, E. E. 1990. Pyruvoyl-dependent enzymes. Annual Review of Biochemistry 59: 29-59.

Willnow, T. E., Hilpert, J., Armstrong, S. A., Rohlman, A., Hammer, R. E., Burns, D. K., and Herz, J. 1996. Defective forebrain development in mice lacking gp330/megalin. Proc. Natl. Acad. Sci. USA 93: 8460-8464.

Xu, M.-Q., and Perler, F. B. 1996. The mechanism of protein splicing and its modulation by mutation. EMBO J. 15: 5146-5153.

Yamada, T., Pfaff, S. L., Edlund, T., and Jessell, T. M. 1993. Control of cell pattern in the neural tube: motor neuron induction by diffusible factors from notochord and floor plate Cell 73: 673-686.

We claim:

1. An in vitro method of identifying a compound that inhibits a hedgehog (hh) response pathway, comprising:
    a) contacting a target cell with a test compound and an hh protein, wherein the test compound is a teratogen, wherein the teratogen is a steroidal alkaloid, and wherein the target cell comprises a hedgehog response pathway that affects an expression level of an hh-target gene, and wherein the target cell is a cell that expresses a patched protein that suppresses the hedgehog pathway in the absence of the hh protein; and
    b) analyzing the expression level of the hh-target gene in the target cell, wherein an expression level of the hh-target gene is reduced as compared to the expression level of the hh-target gene in the absence of the test compound, thereby identifying the test compound as a compound that inhibits hh signaling.

2. The method of claim 1, wherein the target cell is a human cell.

3. The method of claim 1, wherein the steroidal alkaloid is a synthetic teratogen.

4. The method of claim 1, wherein the target cell is a cell from a neural plate explant.

5. The method of claim 1, wherein the hh protein is a recombinant Hedgehog protein.

6. The method of claim 1, wherein the hh protein is Sonic hedgehog (Shh).

7. The method of claim 2, wherein the hh protein is Shh.

8. The method of claim 1, wherein the hh protein comprises the amino-terminal domain of Shh (Shh-N).

9. The method of claim 2, wherein the hh protein is Shh-N.

* * * * *